United States Patent [19]

Burkhart

[11] Patent Number: 5,368,596
[45] Date of Patent: Nov. 29, 1994

[54] AUGMENTED AWL FOR CREATING CHANNELS IN HUMAN BONE TISSUE

[76] Inventor: Stephen S. Burkhart, 201 Village Cir., San Antonio, Tex. 78232

[21] Appl. No.: 64,364

[22] Filed: May 17, 1993

Related U.S. Application Data

[63] Continuation of Ser. No. 853,123, Mar. 18, 1992, abandoned.

[51] Int. Cl.⁵ ............................................. A61B 17/00
[52] U.S. Cl. ...................................... 606/79; 606/205; 606/207; 606/208; 81/300
[58] Field of Search ................ 606/79, 83, 103, 151, 606/163, 165, 174, 175, 205–208; 81/300, 342, 346–348, 350, 351, 427

[56] References Cited

U.S. PATENT DOCUMENTS

| 146,829 | 1/1874 | Lindsay | 81/351 |
|---|---|---|---|
| 148,566 | 3/1874 | Kennedy | 606/184 |
| 321,721 | 7/1885 | Hassan | 806/174 |
| 1,462,202 | 7/1923 | Hopper | 606/207 |
| 1,516,297 | 11/1924 | Isom et al. | 606/208 |
| 1,586,297 | 5/1926 | Du Bois | 81/350 |
| 1,729,265 | 9/1929 | Fitch | 81/351 |
| 2,003,197 | 5/1935 | Jackson | 81/351 |
| 2,327,650 | 8/1943 | Klein | 81/350 |
| 3,090,386 | 5/1963 | Curtis | 128/334 |
| 3,139,089 | 6/1964 | Schwerin | 128/340 |
| 3,181,341 | 5/1965 | Thornton | 81/351 |
| 3,823,719 | 7/1974 | Cummings | 606/208 |
| 3,834,395 | 9/1974 | Santos . | |
| 3,842,840 | 10/1974 | Schweizer . | |
| 3,871,379 | 3/1975 | Clarke . | |
| 3,946,740 | 3/1976 | Bassett . | |
| 4,462,403 | 7/1984 | Martin | 606/83 |
| 4,475,544 | 10/1984 | Reis | 606/208 |
| 4,597,390 | 7/1986 | Mulhollan et al. . | |
| 4,621,640 | 11/1986 | Mulhollan et al. . | |
| 4,760,848 | 8/1988 | Hasson . | |
| 4,836,205 | 6/1989 | Barrett . | |
| 4,890,615 | 1/1990 | Caspari et al. . | |
| 4,898,157 | 2/1990 | Messroghli et al. . | |
| 4,935,027 | 6/1990 | Yoon . | |
| 4,957,498 | 9/1990 | Caspari et al. . | |
| 5,002,554 | 3/1991 | Korber | 606/174 |
| 5,037,433 | 8/1991 | Wilk et al. . | |

FOREIGN PATENT DOCUMENTS

| 0353337 | 9/1905 | France | 606/208 |
|---|---|---|---|
| 0475713 | 9/1913 | France | 81/348 |
| 1225545 | 3/1984 | U.S.S.R. | 606/207 |
| 1618401 | 1/1991 | U.S.S.R. | 606/208 |

Primary Examiner—Stephen C. Pellegrino
Assistant Examiner—Jeffrey A. Schmidt
Attorney, Agent, or Firm—Gunn, Lee & Miller

[57] ABSTRACT

An instrument for determining the location of a channel and for creating a channel through bone tissue for suturing ligament, tendon, or muscle tissue to the bone during arthroscopic surgery, the instrument comprising a pair of compound levers (12) and (14) with handles (18a) and (18b) at a first end (24a) and (24b), a pair of semicircular pincers (36a) and (36b) comprising jaws at a second end (30a) and (30b). The jaws and body of the instrument (10) are inserted through a cannula and adjacent to the bone to be channeled. The jaws are opened to the desired separation, locating the end points (37a) and (37b) on the bone to be channeled and closing the jaws to create the channel.

9 Claims, 3 Drawing Sheets

AUGMENTED AWL FOR CREATING CHANNELS IN HUMAN BONE TISSUE

This is a continuation of copending application(s) Ser. No. 07/853,123 filed on Mar. 18, 1992, now abandoned.

This application incorporates by reference the specification and drawings of U.S. patent application Ser. No. 07/686,132 filed Apr. 16, 1991.

FIELD OF THE INVENTION

A device for locating a channel and for channeling through living human bone tissue, and more particularly a device using an augmented awl with a pair of semicircular pincer comprising jaws thereon.

BACKGROUND OF THE INVENTION

While arthroscopic surgery involving the knee has been practiced for quite some time, arthroscopic surgery on other joints, such as the shoulder, is a relatively new endeavor. A number of problems are encountered in such surgery that are not encountered in arthroscopic surgery of the knee. These problems include working through a thicker layer of skin and muscle tissue than is found in the knee. Other problems include reattaching torn tendons, ligaments, or muscle tissue to bone and the problem of having to work in close proximity to neurovascular structures.

Thus, with such problems, there arises a need for instruments designed to be insertable through a small incision, yet able to reach a remote location at which the repair is to be performed. For example, with the recent advent of arthroscopic surgery to the shoulder, such as in the repair of torn rotator cuff tendons, a new set of instruments and procedures is helpful. As part of the procedure disclosed in the '132 application, a channel (or tunnel) is to be formed in the greater tuberosity of the humerus (shoulder). The traditional method of performing such surgery involves open surgery requiring a large longitudinal wound across the operation site, working through the muscles and exposing the injured tendon. Arthroscopic surgery is preferred, however, especially in view of the quicker recovery time and lessened trauma to the patient. However, arthroscopic surgery requires instruments having a low profile, which are capable of being partially inserted through small incisions in the patient to perform a variety of functions at the operation site located remotely within the patient's body.

In repairing a torn rotator cuff, a channel or tunnel is created through the bone through which suture material can be passed. Presently, such a method of creating a channel employs a pick-type device located at the distal end of a rod. However, problems involved with a pick include the inability to determine exactly where it will emerge when forced through the bone. The "pick method" of creating a channel is, at best, a method of estimating the radius of curvature of the channel and the ultimate end point of the channel where it emerges through the surface of the bone.

What is needed is a device for locating both end points and creating a channel of predetermined radius of curvature between those twin points that can be inserted through a small puncture wound for arthroscopic use. The device of the present invention provides for just such an instrument. More specifically, the device of the present invention provides for a low profile compound lever awl with a pair of semicircular pincer jaws. The use of such a tool allows for a low profile and therefore ease of insertion into the patient, as through a cannula, while also providing for a device to locate and fix the end points of the channel to be created and to positively determine the path of such a channel between the end points.

SUMMARY OF THE INVENTION

The present invention shown in the specifications and described in the claims provides a device for creating a channel through bone tissue for suturing ligaments, tendons, or muscle tissues to the bone during arthroscopic surgery.

The device of the present invention comprises a pair of compound levers with handles at a first end and a pair of semicircular pincers at the second end.

The device of the present invention allows for inserting pincer jaws and the body of the device through a cannula adjacent to the bone to be channeled, opening the jaws to a desired separation by locating the end points of the semicircular pincers against the bone to be channeled and then compressing the jaws.

Thus, the device of the present invention provides for an instrument to create a channel in living human bone tissue.

DETAILED DESCRIPTION OF THE PREFERRED EMBODIMENT

Figure 1:
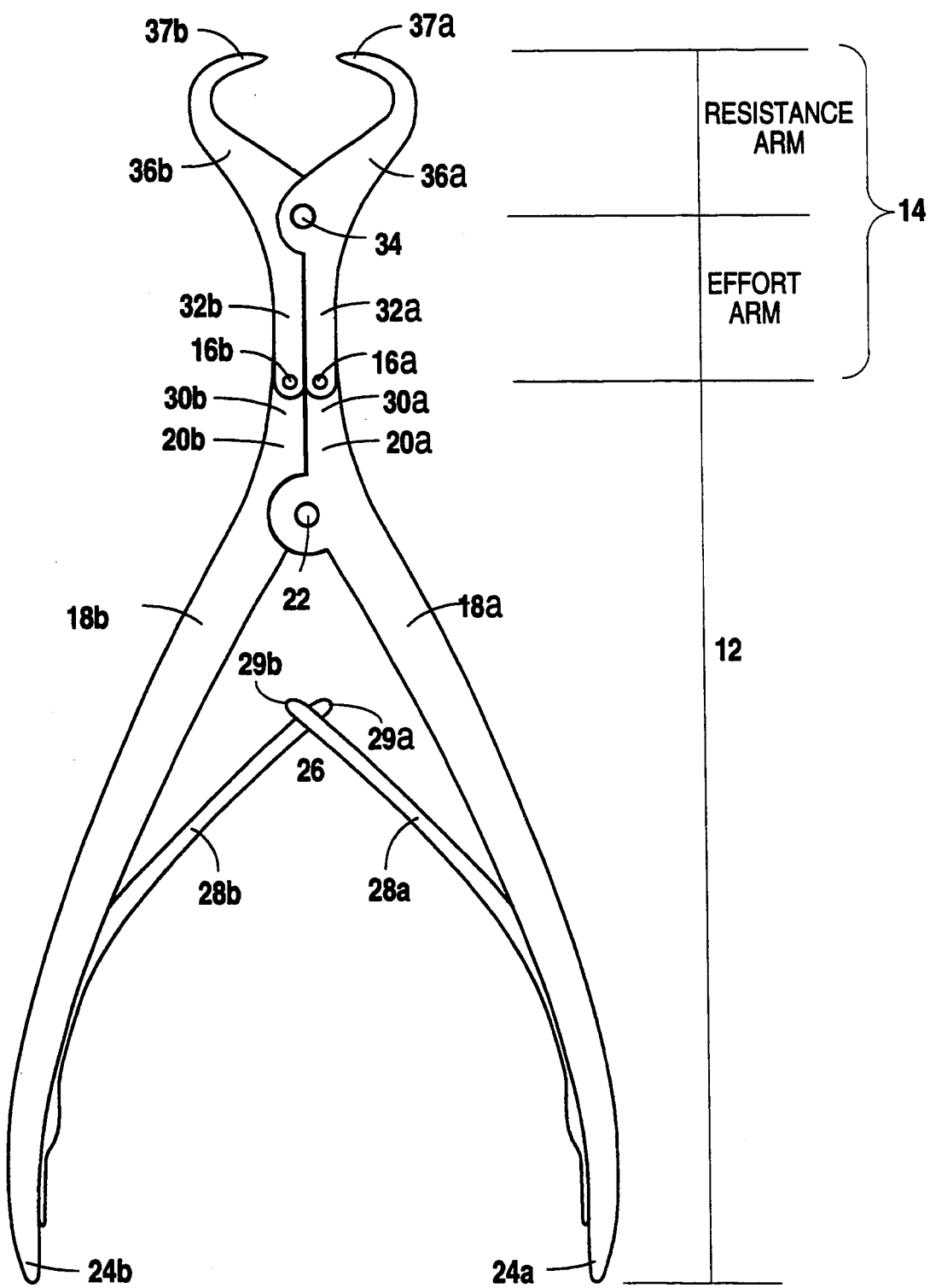
FIG. 1 is a side elevational view of the augmented awl of the present invention with the pincers in an open position against the bone to be channeled.
Figure 2:
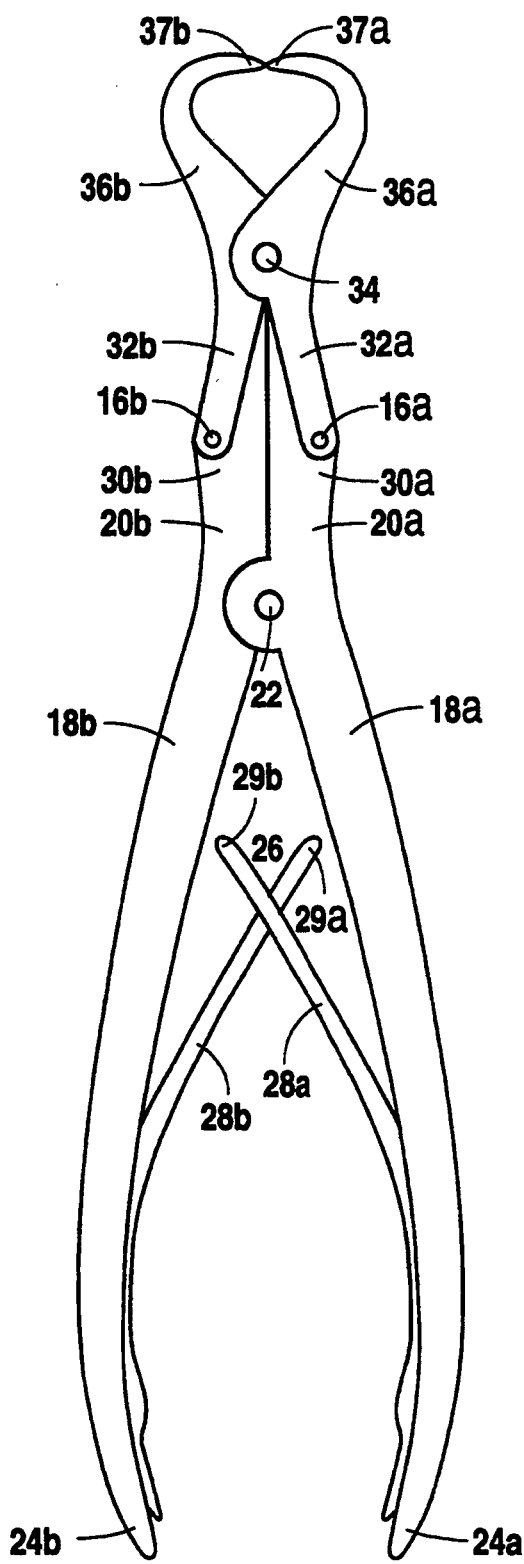
FIG. 2 is a side elevational view of the augmented awl in the present invention with the pincers in the closed position as they would be following channeling through the bone.
Figure 3:
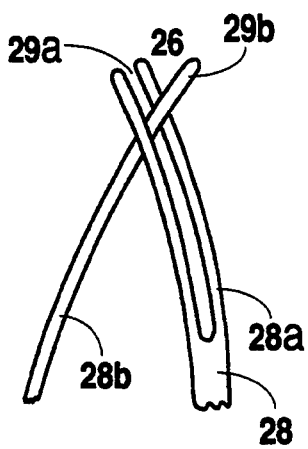
FIG. 3 is a detail view of the means biasing the handles of the augmented awl apart.

FIGS. 1 and 2 illustrate the augmented awl (10) of the present invention. Augmented awl (10) is comprised of first lever pair (12) and second lever pair (14) connected to one another at articulation points (16a) and (16b). First lever pair (12) is comprised of handles (18a) and (18b) which are identically dimensioned and which are integral with resistance arms (20a) and (20b). Handles (18a) and (18b) of first lever pair (12) articulate at first joint (22). Handles (18a) and (18b) have removed ends (24a) and (24b) respectively. Removed ends (24a) and (24b) are held apart, and resistance arms (20a) and (20b) are held in a closed position by use of bias means (26) which may be comprised of leaf springs (28a) and (28b). Leaf springs (28a) and (28b) are fixed at one end to the inside surface of handles (18a) and (18b). At the removed ends of each are a slot (29a) in leaf spring (28a) and a tongue (29b) in leaf spring (28b), the tongue engaging the slot (29a) as illustrated in FIG. 3.

At removed ends (30a) and (30b) of resistance arms (20a) and (20b) are located articulation points (16a) and (16b). Thus, first lever pair (12) is in effect a set of shears at which a compression force applied at removed ends (24a) and (24b) causes articulation at first joint (22) and a force rotating resistance arms (20a) and (20b) outward or apart.

Turning now to second lever pair (14) it can be seen that this is comprised of handle (32a) and (32b) articulating at second joint (34) with resistance arms (36a) and (36b). More particularly, it can be seen that resistance arms (36a) and (36b) are shaped in the form of semicircular pincers which operate together as jaws such that as removed ends (24a) and (24b) are compressed, semicircular pincers (36a) and (36b), with sharp, spike-like tips (37a) and (37b), also compress or close to overcome the resistance generated by the bone. Take note that tips (37a) and (37b) are shaped with beveled edges so that when they close one upon the other, they are slightly adjacent to one another rather than meeting tip to tip, so the tips slightly override (on the beveled edge) one another. This provides for maintenance of sharp tips and for maintenance of uniform width of the bone tunnel.

It can be also seen from FIG. 1 how semicircular pincers have a generally matching and uniform radius of curvature "r" which may be of several sizes preselected by the surgeon depending upon the requirements for the surgical operation. Preferred radii of curvature include: ¾ cm., 1⅛ cm., and 1½ cm., or preferably in the range of ½ cm. to 2 cm. A distance between tips in the range of ½ cm. to 4 cm. is preferable measured when the jaws are in their open position, this range suitable to locate the end points of the tunnel on most adults.

Finally, it should be appreciated that the use of second lever pair (14) provides a means for extending the distance between the applied force at (24a) and (24b) and pincers at resistance arms (36a) and (36b), yet retaining a low profile over the distance through which a portion of the instrument traverses the patient's soft tissues (muscle, fat).

The accompanying table illustrates the combined ideal mechanical advantage resulting on both the force applied on the handles and the distance the handles move when changing the length of the component arms of the first and second pairs of levers.

This table is intended to give the practitioner a summary of the various lengths of lever arms and their effect on distance and force transmitted from handles through to the jaws of the device. However, it is anticipated that the primary function of the device of the present invention is to maintain a low profile instrument while being capable of transmitting a compressive force from the handles through jaws at a removed end thereof.

Figure 4:
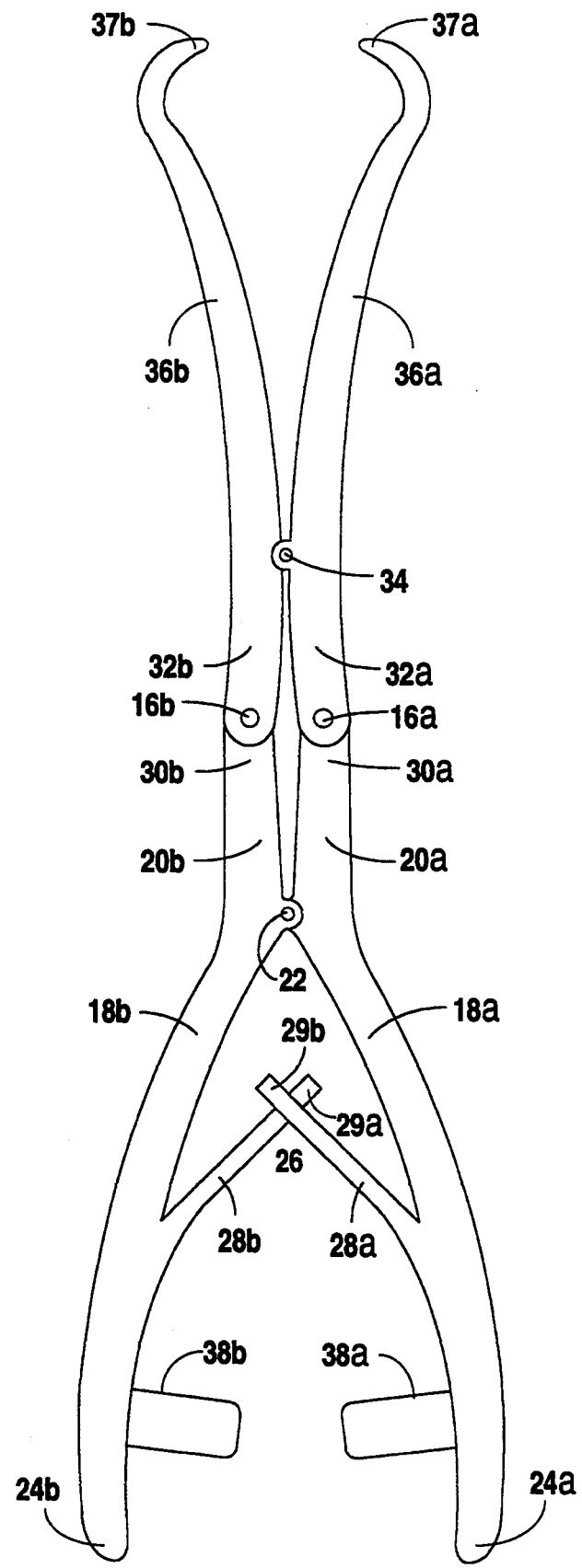
FIG. 4 is a side view of another preferred embodiment of the present invention illustrating a second lever pair having resistance arms substantially longer than effort arms.

Turning now to FIG. 4, it is seen that a preferred embodiment of the present invention is provided with a second lever pair having resistance arms several times longer than the effort arms. This specific embodiment approximates situation a+f, here with $E_1/R_1$, about equal to 4 to 5, and $E_2/R_2$ about equal to ¼ to 1/5, the overall effect being to merely transmit force and distance unchanged. In addition it is seen how awl (10) may be provided with stop means (38a) and (38b). Stop means (38a) and (38b) are provided to prevent the further compression of handles (24a) and (24b) after the jaws reach the closed position. The surgeon will be unable to visually observe the action of the jaw tips as they close as this action will occur inside the bone. However, glancing at stop means (38a) and (38b) will allow the surgeon to estimate the distance remaining between tips (37a) and (37b) or when they have reached the closed position. Stop means (38a) and (38b) are comprised of similarly dimensioned posts oppositely attached to the inside of handles (24a) and (24b). The removed ends of the posts contact as tips (24a) and (24b) contact. This prevents tips (24a) and (24b) from substantially overriding one another.

METHOD OF USE

The instrument is inserted through a speculum sheath or cannula in a position with the jaws closed as illustrated in FIG. 2. This will produce the lowest profile to allow for insertion through the cannula. With the cannula inserted in the patient and the augmented awl of the present invention in a closed position (FIG. 2) and inserted, the surgeon can open the jaws, now past the open mouth of the cannula, and locate the end points of the bone to be channeled, as determined by the requirements of the surgery. With the jaws fully open, the leaf-spring mechanism automatically determines the two end points of the Bone Channel. With the end points so located, the surgeon will apply a gradual compressive force at the handles of the first lever pair, which handles extend well beyond the open mouth cannula and are thus easily grasped by the surgeon. The compressive force applied to the handles will cause the tips of the semicircular pincers to pierce the cortex of the bone. Further compression of the removed ends

TABLE 1

| FIRST LEVER PAIR | | SECOND LEVER PAIR | |
|---|---|---|---|
| LENGTH | EFFECT | LENGTH | EFFECT |
| a. $E_1 > R_1$ | force multiplier/distance reducer | d. $E_2 > R_2$ | force multiplier/distance reducer |
| b. $E_1 = R_1$ | force transmitter only | e. $E_2 = R_2$ | force transmitter only |
| c. $E_1 < R_2$ | distance multiplier/force reducer | f. $E_2 < R_2$ | distance multiplier/force reducer |

Maximum Force Transmitter: a and d, for example:

| if $E_1/R_1 = 3$ and $E_2/R_2 =$ | 2 |
|---|---|
| force multiplier effect = | 6 |
| distance reducer effect = | 1/6 | a + e will transmit whatever force multiplier effect a produces.
a + f will reduce the force multiplier of a by the ratio of $E_2/R_2$.
b + d will transmit without change whatever force multiplier effect $E_2/R_2$ produces.
b + e will transmit the force and distance without change.
b + f will transmit the force reduced and distance multiplied $R_2/E_2$.
c + d will reduce the distance multiplier of c by the ratio of $E_2/R_2$.
c + e will transmit the reduced force, increase distance of c without change. minimum force transmitter, maximum distance multiplier: c + e.

while slowly and gently working the awl in a side to side manner, will provide sufficient force to bring the tips of the pincers together and thereby create the channel. Slowly releasing the compressive force with allow the pincers to withdraw from the channel they have created. Before removal through the cannula, the surgeon will compress the handles to provide for the lowered profile and removal through the cannula.

Terms such as "left", "right", "up", "down", "bottom", "top", "front", "back", "in", "out" and the like are applicable to the embodiment shown and described in conjunction with the drawings. These terms are merely for the purposes of description and do not necessarily apply to the position or manner in which the invention may be constructed or used.

Although the invention has been described in connection with the preferred embodiment, it is not intended to limit the invention to a particular form set forth, but on the contrary, it is intended to cover such alternatives, modifications, and equivalents as may be included within the spirit and the scope of the invention as defined by the appended claims.

I claim:

1. A low-profile instrument for use in arthroscopic surgery, the instrument for creating a channel in living bone tissue, the instrument comprising:
    a first lever pair, each lever of said first lever pair being similarly dimensioned with resistance arms at one end thereof and effort arms at the other end thereof and the levers of said first lever pair articulated at a first joint, the first joint fixedly located between the resistance arm and effort arm of each of said first lever pair, the effort arms of each of said first pair of levers defining handles;
    a second lever pair, the two levers of said second lever pair articulably connected to each other, each one lever of said second lever pair articulably connected with a different single resistance arm lever of said first lever pair;
    said first and said second lever pair in coplanar relation; and
    a pair of semicircular pincers cylindrically shaped sharp pointed, said pair of semicircular cylindrically shaped sharp pointed pincers defining jaws, said jaws integral with said second lever pair for moving between an open position with the jaws apart and a closed position with the jaws together upon actuating the handles of said first lever pair, wherein the jaws lay entirely within the plane of said first and said second lever pair.

2. The instrument of claim 1 wherein the distance between the first joint and the end of the resistance arms of the levers of said first lever pair is less than the distance between the first joint and the end of the effort arms of the levers of said first lever pair.

3. The instrument of claim 1 further comprising means to bias said jaws towards an open position, said bias means integral with the handles of said first lever pair.

4. The instrument of claim 3 wherein said bias means is comprised of a pair of stainless steel leaf springs each having a first end mounted to the inside surface of the handle of said first lever pair and removed ends interlocked, biasing the handles outward and said jaws towards an open position.

5. The instrument of claim 4 wherein each of said pincers of the jaws has the same radius of curvature, the radius of curvature being in the range of ½ cm. to 2 cm.

6. The instrument of claim 5 wherein the maximum height of the instrument seen in profile, with jaws closed, distal to the first joint of said first lever pair is about 3 cm.

7. The instrument of claim 1, 2, 3, 4, 5, or 6 further comprising stop means for preventing the closure of the handles of said first lever pair beyond the closed position of the jaws, said stop means integral with the handles of said first lever pair.

8. A low profile device for use in arthroscopic surgery to create a channel in living bone tissue, the device comprising:
    a first lever pair, each lever of said lever pair being similarly dimensioned with resistance arms at one end thereof and effort arms at the other end thereof and articulated at a first joint, the first joint fixedly located between the resistance arm and effort arm each lever of said first lever pair with effort arms defining handles;
    a second lever pair pivotably connected, one lever to the other, between removed ends thereof, the pair articulably connected to said first lever pair at the effort arms thereof;
    said first and second lever pair in coplanar relation; and
    a pair of semicircular cylindrically shaded, sharp pointed pincers defining jaws, said jaws integral with said second lever pair for moving between an open position with jaws apart and a closed position with jaws together upon compressing the handles of said first level pair wherein said pincers of the jaws each has the same radius of curvature, the radius of curvature in the range of ½ cm. to 2 cm. and wherein the jaws lay entirely within the plane of said first and second lever pair;
    means to bias said jaws towards an open position, said bias means comprising a pair of stainless steel leaf springs, each having a first end mounted to the inside surface of the handle of each of said first lever pairs and having their removed ends interlocked, thereby biasing the handles outward and biasing said jaws in an open position; and
    stop means to prevent the further closure of said handles after reaching the closed position, the stop means comprising a pair of oppositely disposed posts, mounted on the inside of the handles, such that the removed ends of the posts contact one another when the jaws touch.

9. The device as set forth in claim 1, wherein the cylindrically shaped, sharp-pointed pincers are beveled at the points thereof.

* * * * *